(12) United States Patent
Seipel et al.

(10) Patent No.: US 6,723,311 B1
(45) Date of Patent: Apr. 20, 2004

(54) CLEAR, COSMETIC PREPARATIONS CONTAINING FATTY ALCOHOL POLYGLYCOL ETHERS, ETHER SULFATES AND/OR ALK(EN)YL OLIGOGLYCOSIDES, AND METHODS OF PREPARING THE SAME

(75) Inventors: Werner Seipel, Hilden (DE); Hermann Hensen, Haan (DE); Norbert Boyxen, Kempen (DE); Celia Kosboth, Duisburg (DE); Claudia Stammen, Issum (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/857,529

(22) PCT Filed: Nov. 27, 1999

(86) PCT No.: PCT/EP99/09227

§ 371 (c)(1),
(2), (4) Date: Oct. 24, 2001

(87) PCT Pub. No.: WO00/33794

PCT Pub. Date: Jun. 15, 2000

(30) Foreign Application Priority Data

Dec. 8, 1998 (DE) .......................... 198 56 555

(51) Int. Cl.⁷ ..................... A61K 7/06; A61K 7/11; A61K 7/075; A61K 7/08
(52) U.S. Cl. .................. 424/70.11; 424/70.19
(58) Field of Search ................ 424/70.11, 70.19

(56) References Cited

U.S. PATENT DOCUMENTS

| | | | |
|---|---|---|---|
| 3,424,849 A | | 1/1969 | Conklin et al. |
| 4,172,887 A | | 10/1979 | Vanlerberghe et al. |
| 5,656,200 A | * | 8/1997 | Boettcher et al. |
| 5,705,169 A | | 1/1998 | Stein et al. |
| 5,730,960 A | | 3/1998 | Stein et al. |
| 6,193,960 B1 | | 2/2001 | Metzger et al. |

FOREIGN PATENT DOCUMENTS

| | | |
|---|---|---|
| DE | 1 165 574 | 3/1964 |
| DE | 20 24 051 C3 | 10/1979 |
| DE | 44 28 823 A1 | 2/1996 |
| EP | 0 026 073 A1 | 4/1981 |
| EP | 0 300 379 A2 | 1/1989 |
| EP | 0 693 471 A1 | 1/1996 |
| EP | 0 694 521 A1 | 1/1996 |
| EP | 0 818 450 A1 | 1/1998 |
| FR | 2 252 840 | 8/1975 |
| GB | 962919 | 7/1964 |
| GB | 1 333 475 | 10/1973 |

OTHER PUBLICATIONS

Salka, "Alkyl Polyglycosides Properties and Applications", Cosmetics & Toiletries, vol. 108, Allured Publishing Corp., (Mar., 1993), pp. 89–94.

Todd, et al., "Volatile Silicone Fluids for Cosmetic Formulations", Cosmetics & Toiletries, vol. 91, (Jan., 1976), pp. 29–32.

Graham, et al., "Inhibition of the Mitochondrial Oxidation of Octanoate by Salicyclic Acid and Related Compounds", J. Pharm. Pharmac., vol. 26, (1974), pp. 531–534.

Lochhead, et al., "Encyclopedia of Polymers and Thickeners for Cosmetics", Cosmetics & Toiletries, vol. 108, Allured Publishing Corp., (May, 1993), pp. 95–135.

* cited by examiner

Primary Examiner—Sreeni Padmanabhan
Assistant Examiner—San-ming Hui
(74) Attorney, Agent, or Firm—John E. Drach; Aaron R. Ettelman

(57) ABSTRACT

Cosmetic preparations comprising: (a) a mixture of two or more surfactants selected from the group consisting of (a1) fatty alcohol polyglycol ether sulfates, (a2) fatty alcohol polyglycol ethers, and (a3) alk(en)yl oligoglycosides; and (b) one or more oil components; wherein the mixture of surfactants is present in an amount of from 50 to 80% by weight, and the one or more oil components is present in an amount of from 20 to 50% by weight, based upon a total weight of the mixture and the one or more oil components; are disclosed. Also disclosed are methods of preparing such cosmetic preparations.

20 Claims, No Drawings

CLEAR, COSMETIC PREPARATIONS CONTAINING FATTY ALCOHOL POLYGLYCOL ETHERS, ETHER SULFATES AND/OR ALK(EN)YL OLIGOGLYCOSIDES, AND METHODS OF PREPARING THE SAME

BACKGROUND OF THE INVENTION

Prior Art

For the production of cosmetic preparations, surfactants and oils may be mixed with one another in any ratio according to the application envisaged. Hitherto, the corresponding formulations have contained alkanolamides which belong to the "nitrosamine-forming substances". Nitrosamines can have a harmful effect in any quantity, however small, not only through their presence in cosmetics, but also if they enter the body. For this reason, cosmetic preparations with no alkanolamides are desirable. By contrast, the removal of alkanolamides from the surfactant mixtures leads to cloudy formulations on mixing with oil components.

Accordingly, the problem addressed by the present invention was to provide clear, water-free cosmetic preparations which would not turn cloudy, even in storage, by mixing alkanolamide-free surfactant mixtures with defined quantities of oil components.

BRIEF SUMMARY OF THE INVENTION

The present invention relates, in general, to clear, alkanolamide- and water-free cosmetic preparations for use in skin and hair care with a defined content of a mixture of fatty alcohol polyglycol ether sulfates, fatty alcohol polyglycol ethers and/or alk(en)yl oligoglycosides, and one or more oil components.

The present invention also relates to the use of these mixtures for the production of clear, alkanolamine-free cosmetic preparations.

It has surprisingly been found that clear water-free cosmetic preparations can be obtained from cloudy, alkanolamide-free surfactant mixtures consisting of fatty alcohol polyglycol ether sulfates, fatty alcohol polyglycol ethers and/or alkyl and/or alkenyl oligoglycosides by adding a defined quantity of oil components.

DETAILED DESCRIPTION OF THE INVENTION

Fatty Alcohol Polyglycol Ether Sulfates

It is known that alkyl ether sulfates ("ether sulfates") which form component (a1) are anionic surfactants which are industrially produced by the sulfation of fatty alcohol or oxoalcohol polyglycol ethers with $SO_3$ or chlorosulfonic acid (CSA) and subsequent neutralization. Ether sulfates suitable for the purposes of the invention correspond to formula (I):

$$R^1O-(CH_2CH_2O)_nSO_3X \qquad (I)$$

in which $R^1$ is a linear or branched alkyl and/or alkenyl group containing 12 to 18 carbon atoms, n is a number of 1 to 5 and X is ammonium, alkylammonium, alkanolammonium or glucammonium. Typical examples are the sulfates of addition products of on average 1 to 5 and, more particularly, 2 to 3 moles of ethylene oxide onto caproic alcohol, caprylic alcohol, 2-ethyl hexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof in the form of their alkyl, preferably monoisopropanolammonium salts. The ether sulfates may have both a conventional homolog distribution and a narrow homolog distribution. It is particularly preferred to use ether sulfates based on addition products of, on average, 2 to 3 moles of ethylene oxide with technical $C_{12/18}$, preferably $C_{12/14}$ fatty alcohol fractions in the form of their alkyl, preferably monoisopropanolammonium salts.

Fatty Alcohol Polyglycol Ethers

Fatty alcohol polyglycol ethers which form component (a2) are primary aliphatic polyglycol ethers corresponding to formula (II):

$$R^2O(CH_2CH_2O)_mH \qquad (II)$$

in which $R^2$ is a linear or branched, saturated or unsaturated $C_{12-18}$ hydrocarbon radical and m is a number of on average 2 to 6. Typical examples are products of the addition of on average 2 to 6 moles of ethylene oxide onto lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol and elaeostearyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohol. Ethoxylates of technical $C_{12-14}$ fatty alcohols, for example coconut or palm kernel fatty alcohol, are preferred.

Alkyl and/or Alkyl Oligoglycosides

Alkyl and/or alkenyl oligoglycosides which form component (a3) are known nonionic surfactants which correspond to formula (III):

$$R^3O-[G]_p \qquad (III)$$

where $R^3$ is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The overviews presented by Bierman et al. in Starch/Stärke 45, 281 (1993), by B. Salka in Cosm. Toil. 108, 89 (1993) and by J. Kahre in SÖFW-Journal No. 8, 598 (1995) are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (III) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^3$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^3$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Oil Components

Suitable oil components which form component (b) are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Commercial Applications

The cosmetic preparations according to the invention may be used for the production of clear, alkanolamine-free hair and skin care preparations. The preparations such as, for example, hair shampoos, hair lotions, foam baths, shower baths, creams, gels, lotions, alcoholic and aqueous/alcoholic solutions or emulsions, may contain mild surfactants, emulsifiers, superfatting agents, pearlizing waxes, consistency factors, thickeners, polymers, silicone compounds, fats, waxes, stabilizers, biogenic agents, deodorizing agents, anti-dandruff agents, film-formers, swelling agents, UV protection fractors, antioxidants, hydrotropes, preservatives, insect repellents, self-tanning agents, solubilizers, perfume oils, dyes, germ inhibitors and the like as further auxiliaries and additives.

Typical examples of suitable mild, i.e. dermatologically compatible, surfactants are monoglyceride sulfates, mono- and/or dialkylsulfosuccinates, fatty acid isethionates, fatty acid sarcosinates, fatty acid taurides, fatty acid glutamates, ether carboxylic acids, α-olefin sulfonates, fatty acid glucamides, alkyl amidobetaines and/or protein fatty acid condensates (preferably based on wheat proteins).

Suitable emulsifiers are, for example, nonionic surfactants from at least one of the following groups:

(1) products of the addition of 2 to 30 moles of ethylene oxide and/or 0 to 5 moles of propylene oxide onto fatty acids containing 12 to 22 carbon atoms and onto alkylphenols containing 8 to 15 carbon atoms in the alkyl group;

(2) $C_{12/18}$ fatty acid monoesters and diesters of addition products of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) products of the addition of 15 to 60 moles of ethylene oxide onto castor oil and/or hydrogenated castor oil;

(5) polyol esters and, in particular, polyglycerol esters such as, for example, polyglycerol polyricinoleate, polyglycerol poly-12-hydroxysterate or polyglyerol dimerate isostearate. Mixtures of compounds from several of these classes are also suitable;

(6) products of the addition of 2 to 15 moles of ethylene oxide onto castor oil and/or hydrogenated castor oil;

(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(8) mono-, di- and trialkyl phosphates and mono-, di- and/or tri-PEG-alkyl phosphates and salts thereof;

(9) wool wax alcohols;

(10) polysiloxane/polyalkyl polyether copolymers and corresponding derivatives;

(11) mixed esters of pentaerythritol, fatty acids, citric acid and fatty alcohol according to DE 11 65 574 PS and/or mixed esters of fatty acids containing 6 to 22 carbon atoms, methyl glucose and polyols, preferably glycerol or polyglycerol;

(12) polyalkylene glycols and

(13) glycerol carbonate.

Products of the addition of ethylene oxide and/or propylene oxide onto fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic compositions from DE 20 24 051 PS.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau GmbH), quaternized wheat polypeptides, polyethyleneimine, cationic silicone polymers such as, for example, amodimethicone, copolymers of adipic acid and dimethylamino-hydroxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax, hydrogenated castor oils, fatty acid esters solid at room temperature or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts, and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing compositions and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula [Al$_2$(OH)$_5$Cl].2.5H$_2$O and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clay minerals, Pemulen and alkyl-modified Carbopol types (Goodrich). Other suitable polymers and swelling agents can be found in R. Lochhead's review in Cosm. Toil. 108, 95 (1993).

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-dimethylamino)-benzoic acid amyl ester, esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzo-phenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP0 818 450 A1;

propane-1,3-diones such as, for example, 1-(4tert.butylphenyl)-3-(4'-methoxyphenyl)-propane-1,3-dione;

ketotricyclo(5.2.1)decane derivatives, as described in EP 0 694 521

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. So-called micro- or nanopigments are preferably used in sun protection products. Micronized zinc oxide is preferably used.

Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to µmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, ZnSO$_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil. An interesting natural deodorant is the terpene alcohol farnesol (3,7,11-trimethyl-2,6,10-dodecatrien-1-ol) which is present in linden blossom oil and which smells of lily-of-the-valley. Glycerol monolaurate has also been successfully used as a bacteriostatic agent. The percentage content of the additional germ-inhibiting agents is normally about 0.1 to 2% by weight, based on the solids component of the preparations.

The total percentage content of auxiliaries and additives may be from 1 to 50% by weight and is preferably from 5 to 40% by weight, based on the particular composition. The compositions may be produced by standard hot or cold processes and are preferably produced by the phase inversion temperature method.

EXAMPLES

To produce oil baths, different quantities of various oils were added to the alkanolamide-free surfactant formulations (a) to (c):

(a) 75% by weight of fatty alcohol polyglycol ether sulfates (Texapon® Ke 3506, alkanolamide-free, Henkel KGaA) and 25% by weight of fatty alcohol polyglycol ethers (Dehydol® LS 4 DEO-N, Henkel KGaA), (b) 90% by weight of fatty alcohol polyglycol ether sulfates (Texapon® He 3506), alkanolamide-free, Henkel KGaA) and 10% by weight of alkyl oligoglycosides (Plantacare® APG 12000, water-free, Henkel KGaA), (c) 80% by weight of fatty alcohol polyglycol ether sulfates (Texapon® Ke 3506, alkanolamide-free, Henkel KGaA), 10% by weight of fatty alcohol polyglycol ethers (Dehydol® LS 4 DEO-N, Henkel KGaA) and 10% by weight of alkyl oligoglycosides (Plantacare® APG 12000, water-free, Henkel KGaA).

and the oil baths obtained were tested for clouding and shelf life (stable=+, particularly stable=++). The quantity ratios of surfactant to oil used and the results are set out in Table 1. Oil baths 1 to 3 are distinguished by good foam properties.

TABLE 1

Oil baths (composition % by weight

| Composition/ performance | Ratio (surfactant: oil) | 1 | 2 | 3 |
|---|---|---|---|---|
| Cetiol ® A Lauric acid hexyl ester | 70:30 | Crystal clear ++ | Clear + | Clear ++ |
| Cetiol ® HE Polyol fatty acid ester | 50:50 | Clear ++ | Slightly cloudy + | Clear ++ |
| Cetiol ® OE Dioctyl ether | 70:30 | Clear ++ | Crystal clear + | Clear ++ |
| Cetiol ® PGL Hexyl decanol ester of Guerbet alcohol mixtures | 50:50 | Clear ++ | Crystal Clear + | Clear ++ |
| Eutanol ® G Octyl dodecanol Ester | 70:30 | Clear ++ | Crystal clear + | Clear ++ |
| Myritol ® 318 Fatty acid triglyceride | 70:30 | Clear ++ | Clear + | Clear ++ |
| Soya oil | 70:30 | Clear ++ | Crystal clear + | Clear ++ |
| Sunflower oil | 70:30 | Crystal clear ++ | Clear + | Clear ++ |
| Almond oil | 70:30 | Crystal clear ++ | Crystal clear ++ | Clear ++ |

What is claimed is:

1. A cosmetic preparation comprising:
   (a) a mixture of two or more surfactants selected from the group consisting of (a1) fatty alcohol polyglycol ether sulfates (a2) fatty alcohol polyglycol ethers, and (a3) alkyl oligoglycosides and/or alkenyl oligoglycosides, the mixture present in an amount of from 50 to 80% by weight; and
   (b) one or more oil components in an amount of from 20 to 50% by weight; said percentages by weight based upon a total weight of the mixture and the one or more oil components.

2. The cosmetic preparation according to claim 1, wherein the mixture comprises a fatty alcohol polyglycol ether sulfate and one or more components selected from the group consisting of fatty alcohol polyglycol ethers and alkyl oligoglycosides and/or alkenyl oligoglycosides.

3. The cosmetic preparation according to claim 1, wherein the mixture comprises a fatty alcohol polyglycol ether sulfate and a fatty alcohol polyglycol ether.

4. The cosmetic preparation according to claim 1, wherein the mixture comprises a fatty alcohol polyglycol ether sulfate and an alkyl oligoglycoside and/or alkenyl oligoglycoside.

5. The cosmetic preparation according to claim 1, wherein the mixture comprises a fatty alcohol polyglycol ether sulfate, a fatty alcohol polyglycol ether and an alkyl oligoglycoside and/or alkenyl oligoglycoside.

6. The cosmetic preparation according to claim 1, wherein the mixture comprises a fatty alcohol polyglycol ether sulfate of the general formula (I):

$$R^1O-(CH_2CH_2O)_nSO_3X \qquad (I)$$

wherein $R^1$ represents a linear or branched alkyl and/or alkenyl group having from 12 to 18 carbon atoms, n represents a number of from 1 to 5 and X represents a cation selected from the group consisting of ammonium, alkylammonium, alkanolammonium, and glucammonium.

7. The cosmetic preparation according to claim 6, wherein $R^1$ represents a linear alkyl group having from 12 to 14 carbon atoms, n represents a number of from 2 to 3 and X represents alkylammonium.

8. The cosmetic preparation according to claim 1, wherein the mixture comprises a fatty alcohol polyglycol ether of the general formula (II):

$$R^2O(CH_2CH_2O)_mH \qquad (II)$$

wherein $R^2$ represents a linear or branched alkyl and/or alkenyl group having from 12 to 18 carbon atoms, and m represents a number of from 2 to 6.

9. The cosmetic preparation according to claim 8, wherein $R^2$ represents a linear or branched alkyl and/or alkenyl group having from 12 to 14 carbon atoms.

10. The cosmetic preparation according to claim 1, wherein the mixture comprises an alkyl oligoglycoside and/or alkenyl oligoglycoside of the general formula (III)

$$R^3O-[G]_p \qquad (III)$$

wherein $R^3$ represents an alkyl and/or alkenyl group having from 4 to 22 carbon atoms, G represents a sugar unit having 5 or 6 carbon atoms, and p represents a number of from 1 to 10.

11. The cosmetic preparation according to claim 2, wherein the mixture comprises a fatty alcohol polyglycol ether sulfate of the general formula (I):

$$R^1O-(CH_2CH_2O)_nSO_3X \qquad (I)$$

wherein $R^1$ represents a linear or branched alkyl and/or alkenyl group having from 12 to 18 carbon atoms, n represents a number of from 1 to 5 and X represents a cation selected from the group consisting of ammonium, alkylammonium, alkanolammonium, and glucammonium.

12. The cosmetic preparation according to claim 3, wherein the fatty alcohol polyglycol ether sulfate corresponds to the general formula (I):

$$R^1O-(CH_2CH_2O)_nSO_3X \qquad (I)$$

wherein $R^1$ represents a linear or branched alkyl and/or alkenyl group having from 12 to 18 carbon atoms, n represents a number of from 1 to 5 and X represents a cation selected from the group consisting of ammonium, alkylammonium, alkanolammonium, and glucammonium; and wherein the fatty alcohol polyglycol ether corresponds to the general formula (II):

$$R^2O(CH_2CH_2O)_mH \qquad (II)$$

wherein $R^2$ represents a linear or branched alkyl and/or alkenyl group having from 12 to 18 carbon atoms, and m represents a number of from 2 to 6.

13. The cosmetic preparation according to claim 4, wherein the fatty alcohol polyglycol ether sulfate corresponds to the general formula (I):

$$R^1O-(CH_2CH_2O)_nSO_3X \qquad (I)$$

wherein $R^1$ represents a linear or branched alkyl and/or alkenyl group having from 12 to 18 carbon atoms, n represents a number of from 1 to 5 and X represents a cation selected from the group consisting of ammonium, alkylammonium, alkanolammonium, and glucammonium; and wherein the alkyl oligoglycoside and/or alkenyl oligoglycoside corresponds to the general formula (III):

$$R^3O-[G]_p \qquad (III)$$

wherein $R^3$ represents an alkyl and/or alkenyl group having from 4 to 22 carbon atoms, G represents a sugar unit having 5 or 6 carbon atoms, and p represents a number of from 1 to 10.

14. The cosmetic preparation according to claim 5, wherein the fatty alcohol polyglycol ether sulfate corresponds to the general formula (I):

$$R^1O-(CH_2CH_2O)_nSO_3X \qquad (I)$$

wherein $R^1$ represents a linear or branched alkyl and/or alkenyl group having from 12 to 18 carbon atoms, n represents a number of from 1 to 5 and X represents a cation selected from the group consisting of ammonium, alkylammonium, alkanolammonium, and glucammonium; wherein the fatty alcohol polyglycol ether corresponds to the general formula (II):

$$R^2O(CH_2CH_2O)_mH \qquad (II)$$

wherein $R^2$ represents a linear or branched alkyl and/or alkenyl group having from 12 to 18 carbon atoms, and m represents a number of from 2 to 6; and wherein the alkyl oligoglycoside and/or alkenyl oligoglycoside corresponds to the general formula (III):

$$R^3O-[G]_p \qquad (III)$$

wherein $R^3$ represents an alkyl and/or alkenyl group having from 4 to 22 carbon atoms, G represents a sugar unit having 5 or 6 carbon atoms, and p represents a number of from 1 to 10.

15. The cosmetic preparation according to claim 1, wherein the mixture is present in an amount of about 70% by weight, and the one or more oil components are present in an amount of about 30% by weight.

16. The cosmetic preparation according to claim 3, wherein the fatty alcohol polyglycol ether sulfate is present in an amount of about 75% by weight and the fatty alcohol polyglycol ether is present in an amount of about 25% by weight, said percentages by weight based upon a total weight of the mixture.

17. The cosmetic preparation according to claim 4, wherein the fatty alcohol polyglycol ether sulfate is present in an amount of about 90% by weight and the alkyl oligoglycoside and/or alkenyl oligoglycoside is present in an amount of about 10% by weight, said percentages by weight based upon a total weight of the mixture.

18. The cosmetic preparation according to claim 5, wherein the fatty alcohol polyglycol ether sulfate is present in an amount of about 80% by weight, the fatty alcohol polyglycol ether is present in an amount of about 10% by weight and the alkyl oligoglycoside and/or alkenyl oligoglycoside is present in an amount of about 10% by weight, said percentages by weight based upon a total weight of the mixture.

19. A cosmetic preparation comprising:
   (a) a mixture of surfactants comprising a fatty alcohol polyglycol ether sulfate and one or more components selected from the group consisting of fatty alcohol polyglycol ethers and alkyl oligoglycosides and/or alkenyl oligoglycosides, the mixture present in an amount of from 50 to 80% by weight, wherein the fatty alcohol polyglycol ether sulfate corresponds to the general formula (I):

$$R^1O-(CH_2CH_2O)_nSO_3X \qquad (I)$$

wherein $R^1$ represents a linear or branched alkyl and/or alkenyl group having from 12 to 14 carbon atoms, n represents a number of from 2 to 3 and X represents alkylammonium; and
   (b) one or more oil components in an amount of from 20 to 50% by weight; said percentages by weight based upon a total weight of the mixture and the one or more oil components.

20. A method of preparing a clear cosmetic preparation, said method comprising:
   (a) providing a mixture of two or more surfactants selected from the group consisting of (a1) fatty alcohol polyglycol ether sulfates, (a2) fatty alcohol polyglycol ethers, and (a3) alkyl oligoglycosides and/or alkenyl oligoglycosides; and
   (b) combining the mixture with one or more oil components in a ratio by weight of from about 50:50 to about 80:20.

* * * * *